United States Patent [19]
Patterson

[11] 3,967,927
[45] July 6, 1976

[54] DECORATIVE ULTRAVIOLET LAMP FIXTURE

[76] Inventor: Lawrence Patterson, 28745 Berrywood Lane, Farmington Hills, Mich. 48024

[22] Filed: Nov. 25, 1974

[21] Appl. No.: 527,048

Related U.S. Application Data

[63] Continuation-in-part of Ser. No. 514,600, Oct. 11, 1974, which is a continuation-in-part of Ser. No. 374,576, June 28, 1973, Pat. No. 3,846,072.

[52] U.S. Cl. .............................. 21/74 R; 21/102 R; 250/432 R
[51] Int. Cl.² ......................................... A61L 9/00
[58] Field of Search .............. 21/54 R, 74 R, 102 R, 21/DIG. 2; 250/432, 437; 62/78, 264; 240/81 A; 248/356

[56] References Cited
UNITED STATES PATENTS

| | | | |
|---|---|---|---|
| 2,347,954 | 5/1944 | Kiely | 21/102 R X |
| 2,472,243 | 6/1949 | Berryman | 21/74 R X |
| 2,732,501 | 1/1956 | Blaeker | 21/74 R |
| 2,824,343 | 2/1958 | Glass | 21/102 R X |
| 2,979,605 | 4/1961 | Meyerowitz | 240/81 A |
| 3,486,308 | 12/1969 | Burt | 21/74 R X |
| 3,637,342 | 1/1972 | Veloz | 21/102 R |
| 3,757,495 | 9/1973 | Sievers | 21/74 R |
| 3,766,397 | 10/1973 | Rockson | 250/437 X |

OTHER PUBLICATIONS

Nagy et al. "Disinfecting Air with Sterilizing Lamps", Heating, Piping & Air Conditioning 1954, vol. 26, pp. 82-87.
McCulloch "Disinfection & Sterilization", Lea & Febiger, Philadelphia, 1945, pp. 409-412.

*Primary Examiner*—Morris O. Wolk
*Assistant Examiner*—Arnold Turk
*Attorney, Agent, or Firm*—Basile and Weintraub

[57] ABSTRACT

An ultraviolet lamp fixture for purifying the air within a room by means of passing the air over a plurality of hot cathode or other commercially available ultraviolet ray tubes. The tubes are mounted vertically within a decoratively covered, easily movable, pole-mounted housing having a motorized fan which moves air through an opening in the lower portion of the housing over the tubes for purification. The purified air stream is exhausted through the top portion of the housing and returned to the room. The interior of the housing has deflector vanes which function to create a turbulent air flow in the area of the tubes to insure that all of the air passing through the lamp fixture is purified by contacting the lamps. The lamp fixture is provided with means for filtering the circulating air. In an alternate embodiment, the air passes through a dehumidifier prior to passing by the tubes.

5 Claims, 4 Drawing Figures

DECORATIVE ULTRAVIOLET LAMP FIXTURE

CROSS REFERENCE TO RELATED PATENT APPLICATIONS

The present application is a continuation-in-part of copending U.S. patent application Ser. No. 514,600 filed 10-11-74 which, in turn, is a continuation-in-part of U.S. patent application Ser. No. 374,576, filed 6-28-73 and now U.S. Pat. No. 3,846,072, issued 11-5-74.

BACKGROUND OF THE INVENTION

I. Field of the Invention

The present invention relates to an easily movable, aesthetically pleasing means for purifying air within a room and, specifically, to an air purifying means which can be easily and temporarily fixed at various locations around the room.

II. Description of the Prior Art

The germicidal effects of ultraviolet ray tubes due to their emitting radiation is well known and their use has been proposed in various applications. Examples of such ultraviolet lamps are disclosed in U.S. Pat. Nos. 2,248,618; 2,347,254; 2,350,462; 2,407,379; 2,732,501, 3,107,863 and 3,674,421.

In certain of the apparatuses disclosed in the aforementioned United States patents, ultraviolet ray tubes are employed for bactericidal radiant energy, and these tubes are supported in fixtures suspended directly above the zone which is desired to be sterilized. Purification is obtained by direct exposure to the light emitted from the tubes. In some of the prior art apparatuses persons within the zone of sterilization must usually protect their eyes from the rays of the tube, or special reflective coatings bouncing off the radiation must be provided. These types of apparatuses are necessarily limited to the sterilization of very small areas and suitable only for a particular situation and location as the effectiveness of the ultraviolet ray is greatly minimized if any obstructions are placed between the objects to be purified and the ultraviolet tube. One place where a large concentration of pathogens are formed is in a doctor's office wherein one could not practically house any of these previously disclosed fixtures because of inhabitants' fear of exposure to the rays from the tubes. Further, the effects of the ultraviolet germocidal features are greatly minimized beyond one meter from the tube. Additionally, none of the previously disclosed art claim the aesthetic design of the present invention, such design positively assuring marketability and actual effective use in providing purified air in a location such as a doctor's office.

In my aforementioned patents and patent application, it was suggested that certain of the aforementioned disadvantages may be overcome by providing a means for circulating the air within a room through a fixture by means of a fan or the like so that all the air passes over the tubes in closer proximity thereto, thus obtaining a maximum exposure to the ultraviolet tubes and a maximum kill of the airborne micro-organisms. Although the apparatuses disclosed in the aforementioned United States patents may with various degrees of success function to destroy airborne micro-organisms, they have disadvantages in their use and application, namely, lack of protection from harmful rays and lack of aesthetic appearance reflecting on poor marketability, all of which are overcome by the present invention.

SUMMARY OF THE INVENTION

The present invention which will be described subsequently in greater detail comprises an ultraviolet light fixture concealed by a decorative covering and mounted on a pole providing flexibility of location and means for forceably moving air in a turbulent fashion over an ultraviolet tube for the purification and exhausting of the air back into the room.

It is therefore an object of the present invention to provide a new and improved ultraviolet lamp fixture which is simple in its construction and inexpensive to manufacture, yet one which will function to purify air in a room to remove any airborne micro-organisms and which is provided with means for insuring that all of the air exhausted from the fixture is purified.

It is also an object of the present invention to provide an ultraviolet lamp fixture having means for facilitating the easy movement of the fixture so that the fixture position can be changed within a room.

It is also an object of the present invention to provide an ultraviolet lamp fixture which is aesthetically pleasing in appearance by means of a decorative covering which conceals the housing of the fixture and shields the ultraviolet tubes of the fixture from the eyes of persons in a room with the operating fixture, such aesthetic quality encouraging and promoting actual use of such a beneficial light fixture in an appropriate setting such as a doctor's office.

It is still a further object of the present invention to provide an ultraviolet lamp fixture having means for dehumidifying the air prior to passing the air over the ultraviolet tubes.

Other objects, advantages, and applications of the present invention will become apparent to those skilled in the art of decorative ultraviolet lamp fixtures when the accompanying description of one example of the best mode contemplated for practicing the invention is read in conjunction with the accompanying drawing.

BRIEF DESCRIPTION OF THE DRAWING

The description herein makes reference to the accompanying drawing wherein like reference numerals refer to like components throughout the several views, and in which.

Figure 2:
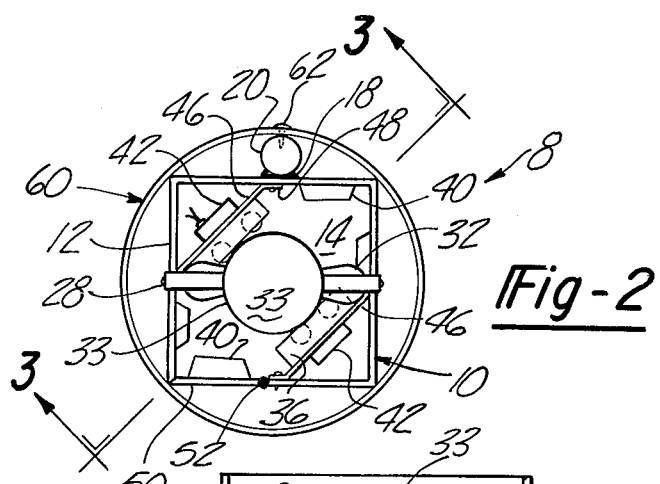
FIG. 2 is a top elevational view of the ultraviolet lamp fixture illustrated in FIG. 1.
Figure 1:
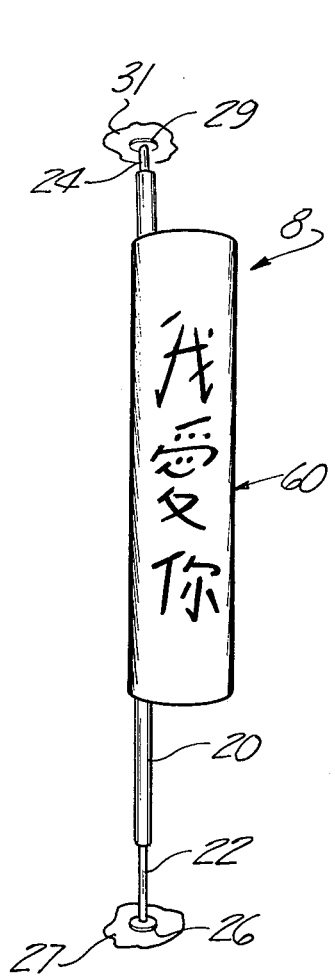
FIG. 1 is a perspective view of a free standing ultraviolet lamp fixture constructed in accordance with the principles of the present invention.
Figure 3:
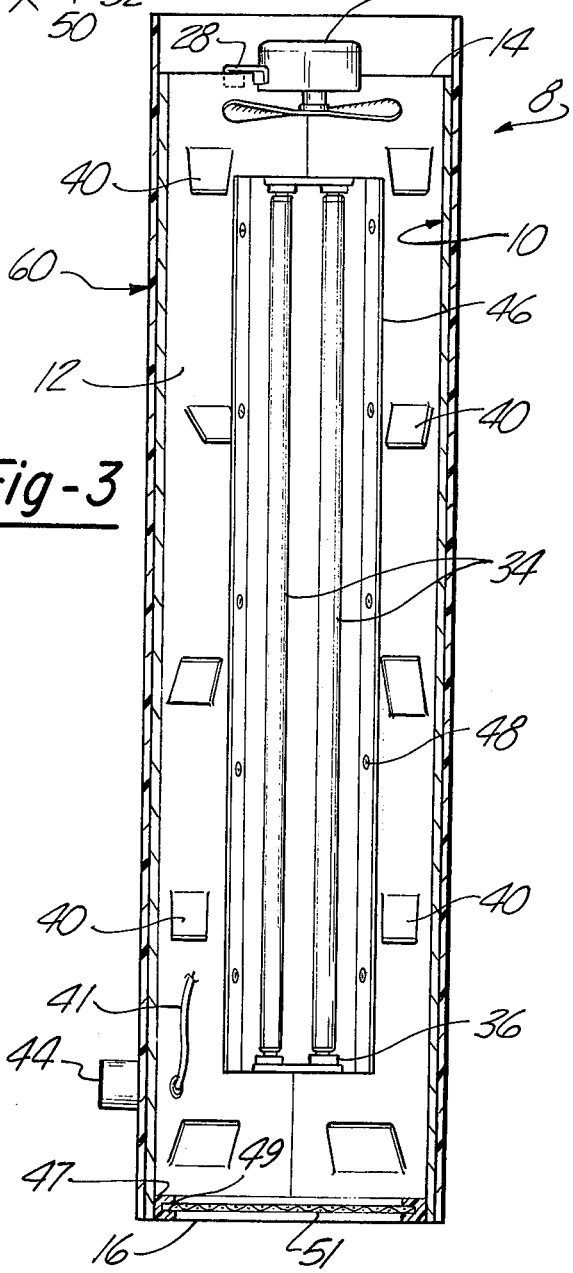
FIG. 3 is an enlarged longitudinal cross-sectional view of the ultraviolet lamp fixture taken along line 3—3 of FIG. 2.

Referring now to the drawing and, in particular, to FIGS. 1, 2 and 3 wherein there is illustrated an example of the present invention in the form of an ultraviolet lamp fixture 8 comprising a rectangularly shaped housing 10 having side walls 12, a top opening 14, and a bottom opening 16. The housing 10 is affixed to a pole 20 by any suitable means such as by welding at 18. The lower end of pole 20 carries a support rod 22 attached thereto by any suitable means and ending in a disc 26 which permits the pole 20 to stand on the floor 27. The top portion of pole 20 telescopically receives a support rod 24 having a disc shaped end 29 which is adopted to abut the ceiling 31 of the room. A spring (not shown) carried by the pole 20 and acting against the support rod 24 assures a sufficient tension between the support rod 24 and the ceiling 31 to maintain the fixture 8 in the upright position shown in FIG. 1. At the same time, such tension provides an easy means of changing the placement of the fixture 8 in the room.

The housing 10 may be fabricated from any suitable material and, preferably, the housing 10 is fabricated from sheet metal with the various sides being fastened to each other in a constitutional manner, that is, with threaded fastners or welding or the like, all of which is not described in detail as such fastening means do not pertain to the present invention and are well known to those skilled in the art of fabricating comparably shaped housings and the like from sheet metal and like materials.

A propeller type fan 32 driven by an electric motor 33 is attached to the housing 10 by means of a mounting bracket 28. The fan 32 is adapted to draw air into the bottom opening 16, of the housing 10, and exhaust the air through the top opening 14 into the room.

As can best be seen in FIG. 3, the interior of the housing 10 is also provided with a plurality of vane elements 40 which are attached to the side walls 12 of the housing 10 so as to provide a deflection of the inflowing air thereby relating a turbulent air flow past a plurality of ultraviolet ray tubes 34 that are carried within the housing 10. The plurality of ultraviolet ray tubes 34 are longitudinally mounted within the central portion of the housing 10 and are so spaced from one another and from the walls of the housing 10 that substantially all of the air passing through the interior of the housing 10 will pass over at least one of the tubes 34. The turbulent effect generated by the deflecting vane elements 40 insures that the air will pass by one or more tubes 34 such that any disease bearing organisms carried by the air will pass within close proximity to one or more of the ultraviolet tubes 34 whereby the ultraviolet light emitted by the tubes 34 will kill such disease carrying organisms.

The ultraviolet ray tubes 34 are mounted in two opposing sets of sockets 36 which are electrically connected by suitable electrical wiring 41 to ballast 42 and an off/on switch mounted in control box 44. The fan motor 33 is also electrically connected to the control box 44 permitting co-operation of the propeller fan 32 and the ultraviolet ray tubes 34.

The sets of sockets 36 are located on both ends of tube mounting brackets 46 which are rectangular shaped and attached to the inside surface of walls 12 of the housing 10 by means of screws 48 or the like.

A pair of opposing brackets 47 having longitudinal slots 49 are carried by the housing side walls 12 adjacent to the bottom opening 16. The slots 49 slidably support a filter element 51 which filters the air moving into the housing 10 through bottom opening 16. An aperture, not shown, in the housing side wall 12 provides an easy means for removing and replacing the filter. Such filters are commercially available and are particularly adapted to remove pollen and other air-borne material from the air to further purify the same.

A door 50 hinged at 52 on a side wall 12 and running the length of the housing 10 provides an entry to the interior of the housing 10 for the purpose of cleaning and replacing the ultraviolet ray tubes 34. Such cleaning is necessary since dust around an ultraviolet ray tube 34 could function to limit the effective kill rate of the ultraviolet radiation as such radiation cannot penetrate dust to any degree.

Figure 4:
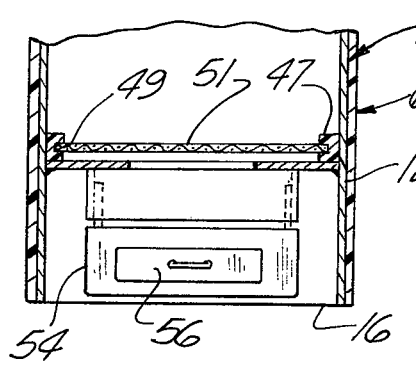
FIG. 4 is an alternate embodiment of the ultraviolet lamp fixture illustrated in FIG. 3.

In FIG. 4 an alternate embodiment is illustrated as comprising a dehumidifier 54 which is carried by the side walls 12 below brackets 47 which, in turn, hold a filter 51. The dehumidifier 54 serves to reduce the relative humidity of the air passing through the bottom opening 16 into the central chamber of the housing 10 to a factor which is less than 70% relative humidity. Water collected by the dehumidifier 54 is stored in a drawer 56 located in the lower portion of the dehumidifier 54. Thedehumidifier 50 is electrically connected to the control box 44 in a conventional manner known to those skilled in the art of electrical devices. The connection is designed so that the dehumidifier 54 co-operates simultaneously with the ultraviolet ray tubes 34 and the propeller fan 32.

A decorative cylinder shaped covering 60 wraps around the housing 10 and pole 20 and fastens to the pole 20 by means of snap in type screws 62 or any other suitable fastening device which permits easy removal of the covering 60 from the pole 20 to provide for easy access to the housing 10. Such decorative covering may be fashioned from any suitable material, one example being plastic.

In use, the ultraviolet lamp fixture 8 is positioned anywhere in a room by means of the tension exerted on the pole 20 by a spring contained therein. The fixture 8 is actuated such that the motor 33 is operable to drive the fan 32 which functions to draw air in through the bottom opening 16 and through the air filter 51 whereby impurities are removed from the air. As the air continues to move upward through the interior of the housing 10 deflector vane elements 40 act to create a turbulence. As the turbulent air passes by each of the ultraviolet tubes 34, the micro-organisms carried by such air should pass in close proximity to at least one and preferably several of the tubes 34 whereby an effective kill may be had. Such turbulence is necessary to offset the speed of the air movement through the housing 10. The slower moving air is thus subjected to surface contact with the ultraviolet tubes 34. This surface contact exposure has been proven by scientific evaluation to contain 300 times the killing factors present or attending at a one meter exposure. By providing tubes 34 of a high intensity and by assuring that the turbulent air within the cabinet makes several passes by each tube 34, the micro-organisms should be effectively killed.

It can thus be seen that the present invention has provided a new and improved germocidal lamp fixture which has numerous advantages over the prior art structure in that the lamp fixture can be located at numerous sites in a room and easily moved from one place to another.

It can also be seen that the present invention provides a means for preparing air such that the same may be filtered and subjected to substantial ultraviolet radiation in a most optimum manner whereby the organisms carried by the air are subjected to high intensity ultraviolet radiation several times and, if desired, in an optimum relative humidity condition.

In addition, the decorative covering 60 which encloses the housing 10 insures that persons in a room where such ultraviolet light fixture 8 is positioned will not have to protect their eyes from the rays of the tubes as is normally required.

Although only one example of the present invention has been disclosed, it should be understood by those skilled in the art of ultraviolet lamp fixtures that other forms may be had all coming within the spirit of the invention and the scope of the appended claims.

What is claimed is as follows:

1. An ultraviolet lamp fixture for purifying the air within a room, said fixture comprising:

a floor-to-ceiling tension supported pole;

a housing having a plurality of upright side walls;

means fastening a first of said housing walls to said tension supported pole such that said housing is supported in an upright position when said tension supported pole is positioned between a floor and a ceiling;

the lower portion and the upper portion of said housing being opened and respectively defining an air brake and an air outlet with the interior of said housing defining an air passageway between said air inlet and said air outlet;

a motorized fan releasably supported at said housing outlet for drawing air through said air intake into the interior of said housing and exhausting said air through said air outlet defined at the top of said housing;

means releasably securing said motorized fan between a pair of opposing side walls defining said housing;

a plurality of ultraviolet ray tubes mounted in said housing in said air passageway between said air inlet and said air outlet;

bracket means attached to adjacent side walls of said housing for supporting said tubes in an upright fashion in said air passageway;

a portion of a second of said side walls of said housing being pivotally attached to said housing to define an access door of a length at least equal to the length of said tubes to permit access to the interior of said housing to permit the dusting of the outer surfaces of said ultraviolet ray tubes without removing said tubes from said housing;

a circular decorative covering opened at opposite ends and encircling said housing and concealing the same, said cover being slidably movable with respect to said housing to permit removal of said covering from said housing to gain access to said door; the space between said first-mentioned side wall of said housing and the opposing inner surface of said decorative cover being of a sufficient distance to permit the passage of said tension supported pole; said decorative cover being releasably secured to said tension pole at spaced locations opposite said first-mentioned side wall.

2. The ultraviolet lamp fixture defined in claim 1 further comprising filter means removably attached to said housing at said air intake end of said housing to facilitate the replacement of said filter means, said filter means trapping pollen and dust and the like to remove the same from the airstream passing into the interior of said housing through said air intake.

3. The ultraviolet lamp fixture defined in claim 1 further comprising means disposed in said air passageway for deflecting said air flow and generating a turbulent air flow by said ultraviolet ray tubes.

4. The ultraviolet lamp fixture defined in claim 3 wherein said last-mentioned means comprises a plurality of punched-out portions of said side walls forming vanes disposed in the path of said airstream.

5. The ultraviolet lamp fixture defined in claim 1 further comprising means for dehumidifying the air prior to the passage of said air by said ultraviolet ray tubes.

* * * * *